US00PP36025P2

(12) United States Plant Patent
Aguilar Morán

(10) Patent No.: US PP36,025 P2
(45) Date of Patent: Jul. 23, 2024

(54) DESSERT BANANA PLANT NAMED 'WW01'

(50) Latin Name: *M. acuminata*
Varietal Denomination: WW01

(71) Applicant: Fundación Hondureña de Investigación Agrícola (FHIA), San Pedro Sula (HN)

(72) Inventor: Juan Fernando Aguilar Morán, La Lima (HN)

(73) Assignee: Fundación Hondureña de Investigación Agrícola (FHIA) (HN)

( * ) Notice: Subject to any disclaimer, the term of this patent is extended or adjusted under 35 U.S.C. 154(b) by 0 days.

(21) Appl. No.: 18/469,766

(22) Filed: Sep. 19, 2023

(51) Int. Cl.
*A01H 5/08* (2018.01)
*A01H 6/00* (2018.01)

(52) U.S. Cl.
USPC ..... Plt./160
CPC ..... *A01H 6/00* (2018.05)

(58) Field of Classification Search
USPC ..... Plt./160
CPC ..... A01H 5/08
See application file for complete search history.

*Primary Examiner* — Kent L Bell
(74) *Attorney, Agent, or Firm* — Garvey, Smith & Nehrbass, Patent Attorneys, L.L.C.; Seth M. Nehrbass; Fabian M. Nehrbass

(57) ABSTRACT

The 'WW01' is a hybrid dessert banana variety with a medium-sized stature, is tolerant to Black Sigatoka, and produces high-quality fruit.

6 Drawing Sheets

Latin name of the genus and species of the plant claimed: This tetraploid plant has only *Musa acuminata* in its pedigree and is the product of an inter-specific cross between triploid (AAA) plants of the same cultivar. The Latin name of 'WW01' is *M. acuminata*, tetraploid (AAAA), representing four genomes of this genus and species.

Variety denomination:
'WW01'.

CROSS-REFERENCE TO RELATED APPLICATIONS

This application is co-pending with the following additional applications by the same inventor: "DESSERT BANANA PLANT NAMED 'SH-4199'" (application Ser. No. 18/469,772); "DESSERT BANANA PLANT NAMED 'NW02'" (application Ser. No. 18/469,776); "DESSERT BANANA PLANT NAMED 'WH02'" (application Ser. No. 18/469,781); and "DESSERT BANANA PLANT NAMED 'HG07'" (application Ser. No. 18/469,787). The plants of these applications, as well as the plant of the present application, were created in the banana breeding program of Applicant/Owner/Assignee, FHIA.

STATEMENT REGARDING FEDERALLY SPONSORED RESEARCH OR DEVELOPMENT

Not applicable.

BACKGROUND OF THE INVENTION

This invention relates to a new and distinctive hybrid banana variety named 'WW01'. This new hybrid variety was the result of a field cross performed in 2016 in La Lima Cortés, Honduras, between 'Williams' x 'Williams' (Both unpatented). 'Williams' is a medium-sized triploid plant (AAA) susceptible to Black Sigatoka leaf spot disease (*Mycosphaerella fijiensis*), belonging to the Cavendish group. 'Williams' is one of the most commercialized bananas worldwide; people prefer it for its flavor, aroma, and size. This banana was selected from a germplasm collection.

'WW01' is a tetraploid hybrid (AAAA) created for the genetic improvement of the Cavendish group banana. This hybrid was selected in 2018 from several first-generation seedlings from the cross between 'Williams' x 'Williams.' It was chosen as a tetraploid hybrid maintaining the "Cavendish type" stature of its female parental line and producing bunches of 20 kilograms with fruits of the same quality as its parents. 'WW01' was asexually reproduced by corms by the breeder in La Lima Cortes, Honduras. All plants and fruit run true to the initially selected plant and are identical in all aspects.

The hybrid 'WW01' has the same plant as male and female ('Williams'). Its characteristics of plant height, type of leaves, type of stem, and number of offspring are like those of its parents. However, the stem color, bunch type, and taste are different. The 'WW01' hybrid has not inherited the delightful flavor that the 'Williams' variety, belonging to the Cavendish subgroup, is known for. This hybrid has lush foliage, which appears to be more resistant to black Sigatoka than its parents. These comparisons are valid when comparing commercial varieties known to the Inventor because the 'Williams' variety is one of the most commercialized in the world.

BRIEF SUMMARY OF THE INVENTION

The 'WW01' is a hybrid dessert banana variety with a medium-sized stature, is tolerant to Black Sigatoka, and produces high-quality fruit.

BRIEF DESCRIPTION OF THE PHOTOGRAPHS

The figures describe the characteristics of the 'WW01' hybrid banana variety. The color shown in the photographs is as nearly accurate as reasonably possible in this type's color representation.

FIG. 1 shows the typical appearance of a plant at ten (10) months old;

FIGS. 2A-B shows blotches at the petiole base (A) and a petiole canal leaf (B);

FIGS. 3A-C shows the shape of a leaf blade base (A) and leaf upper (B) and leaf lower (C) surfaces;

FIG. 4 shows typical suckers;

Figure 1:
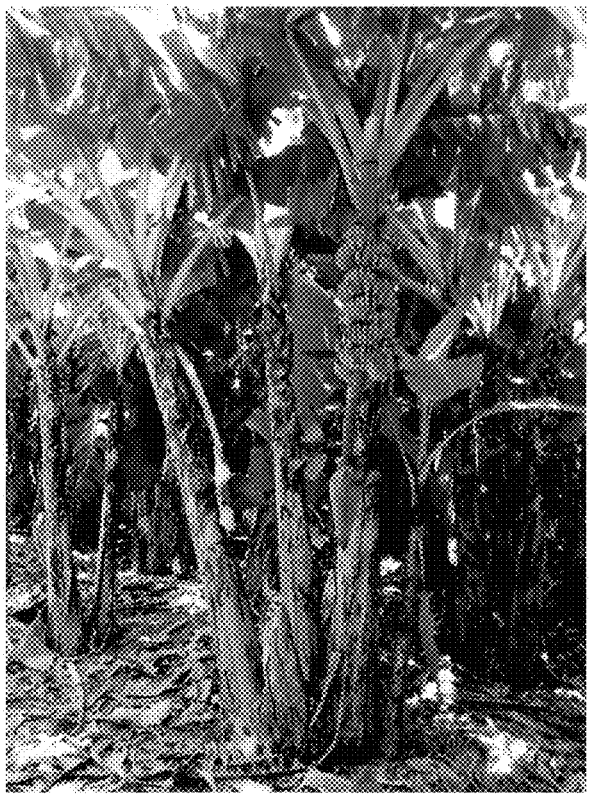
Figures 2A, 2B:
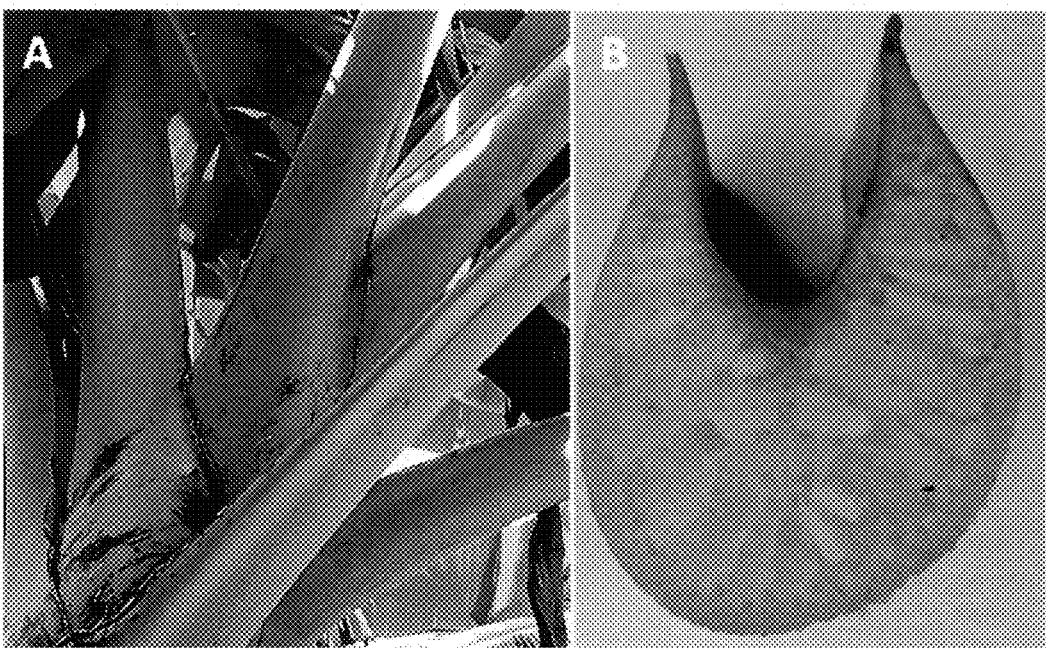
Figure 5:
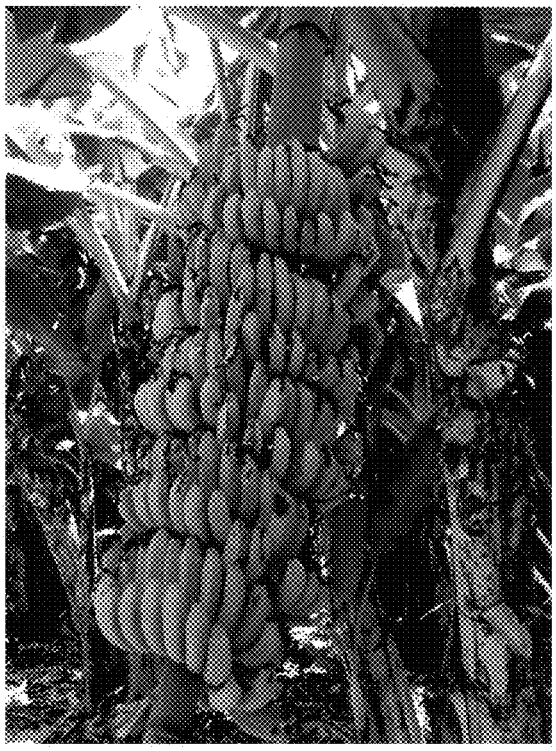
FIG. 5 shows a typical fruit bunch.
Figure 6:
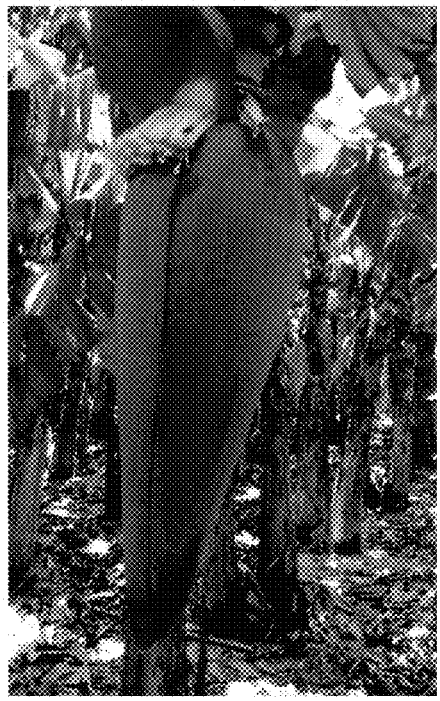
FIG. 6 shows a male bud.
Figure 8A:
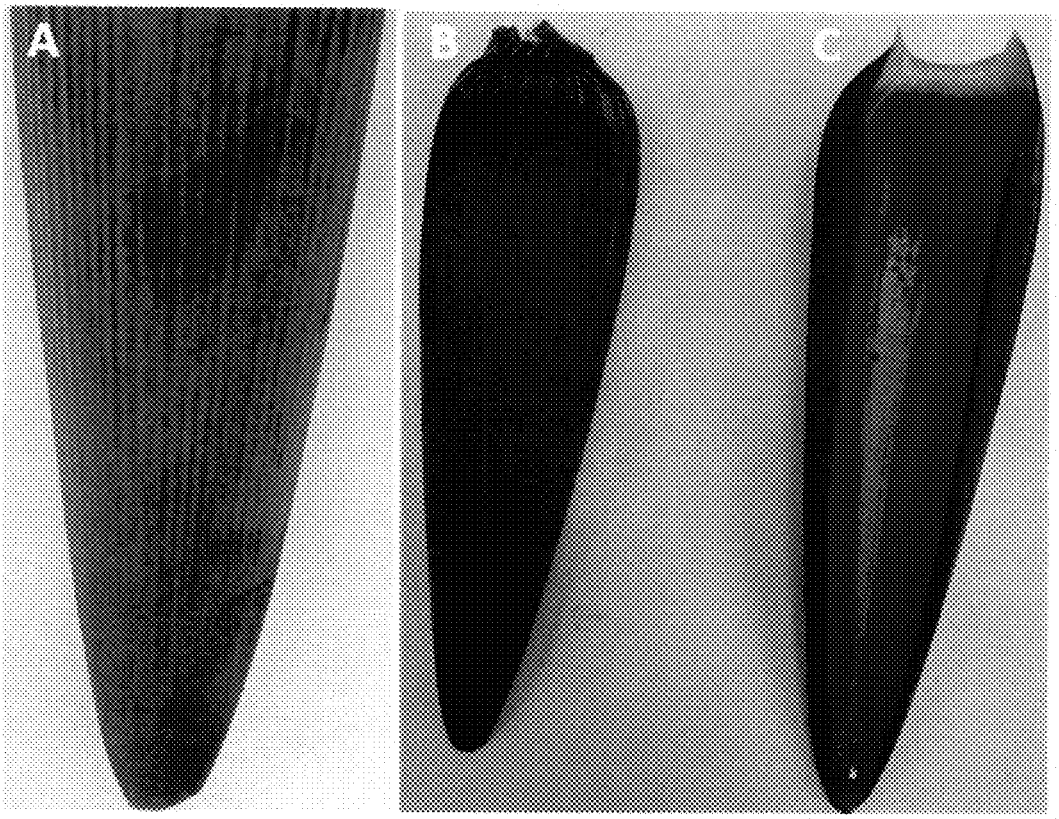
Figure 8B:
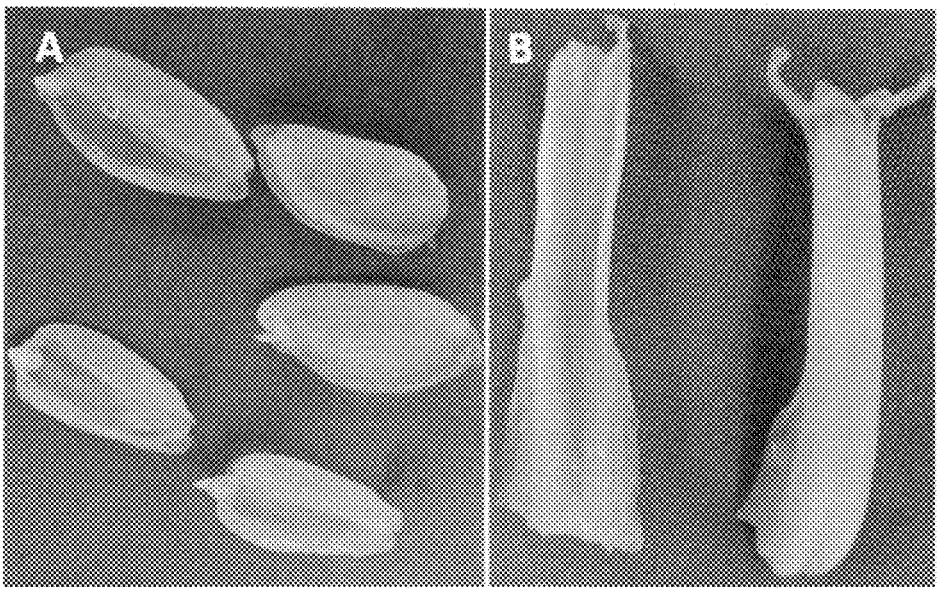
Figures 9A, 9B:
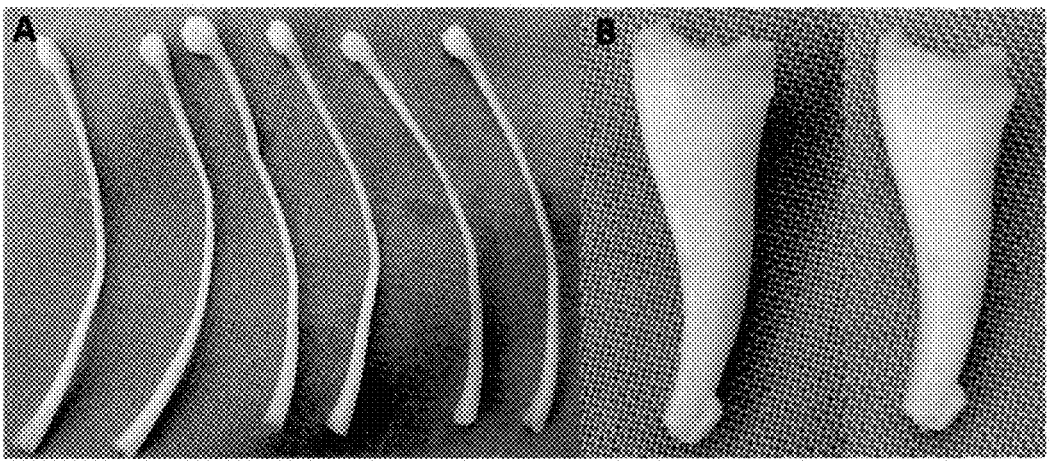
Figure 10:
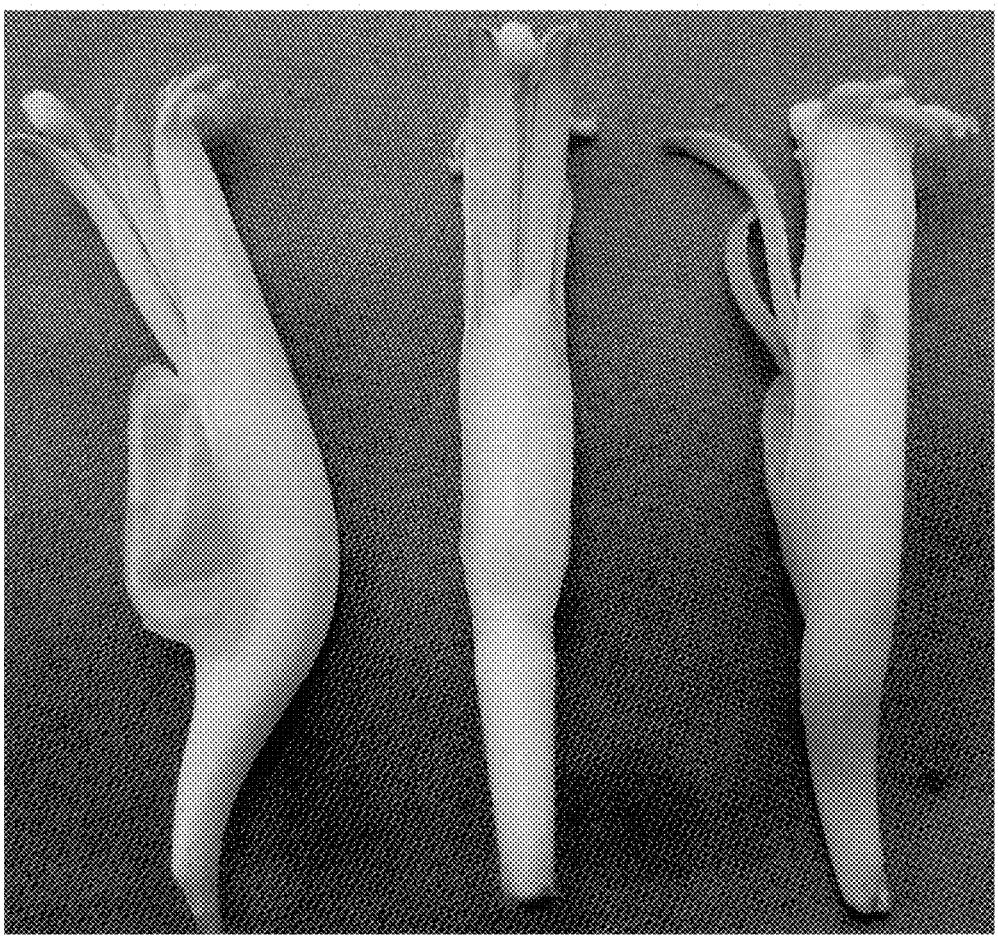
Figure 11:
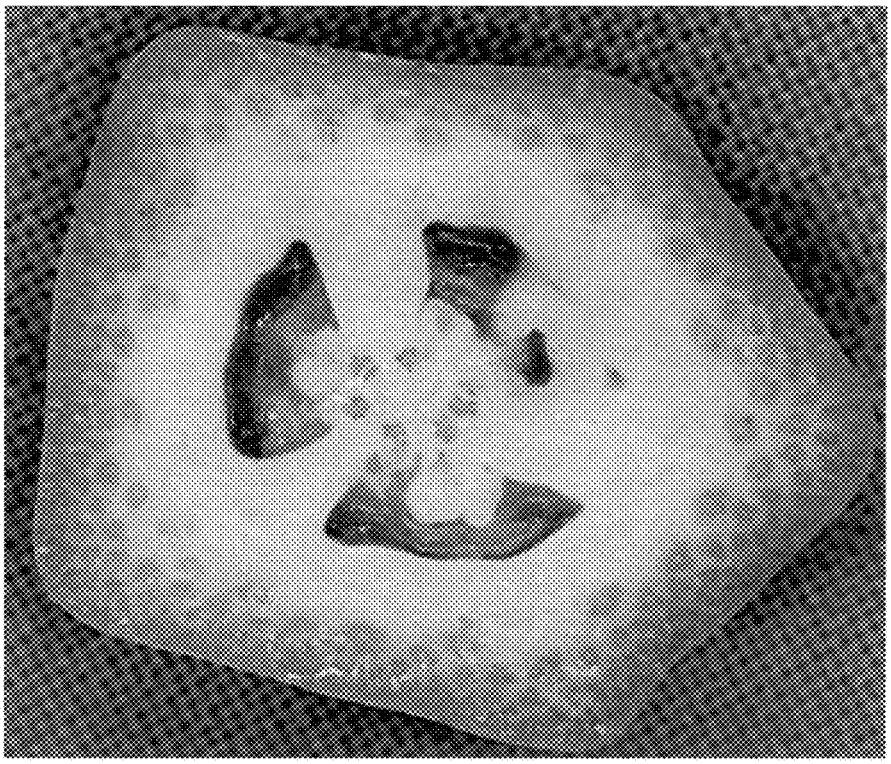

FIGS. 7A-C shows bracts of a male bud;

FIGS. 8A-B shows lopes of compound tepals (A) and free tepals (B);

FIGS. 9A-B shows style shape (A) and ovary (B);

FIG. 10 shows a male flower;

FIG. 11 shows rowed ovules; and

Figure 12:
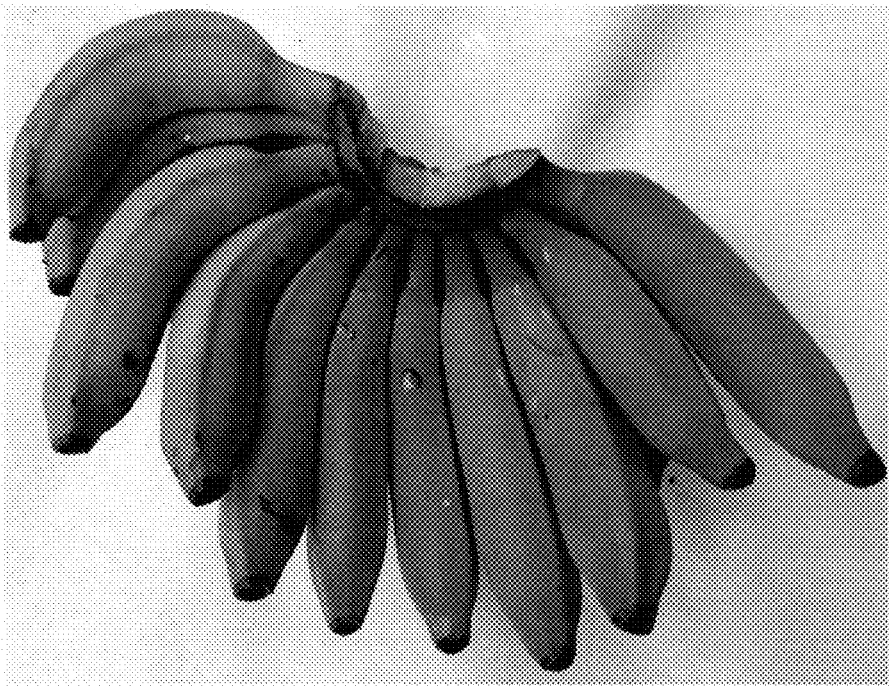

FIG. 12 shows a typical second hand.

DETAILED BOTANICAL DESCRIPTION

The following is a detailed botanical description of the new variety 'WW01'. The report is from ten-month old plants in La Lima, Cortés, Honduras that were evaluated in 2023. The descriptions concord with the internationally standardized "Descriptors for Banana (*Musa* spp.)" elaborated by IPGRI/INIBAP/CIRAD, 1996 (www.inibap.org), and The U.K.'s Royal Horticultural Society's Color Chart, 2001. The 'WW01' plant and its fruit may vary slightly from the detailed descriptors shown below due to cultural practices, soil types, and climatic conditions under which the variety may be cultivated.

| | |
|---|---|
| Leaf habit | Drooping |
| Dwarfism | Not shown |
| Pseudostem length | 2.60 meters |
| Pseudostem width | 63 cm |
| Pseudostem height | 2.1 to 2.9 meters |
| Pseudostem aspect | Robust |
| Pseudostem color | Green (143C, RHS) |
| Pseudostem appearance | Shiny (Not waxy) |
| The predominant underlying color of the pseudostem | Green (142D, RHS) |
| Pigmentation of the underlying pseudostem | Brown (N200A, RHS) |
| Sap color | Milky (150D, RHS) |
| Wax-on leaf sheaths | Moderately wax |
| Number of suckers | 3 to 5 |
| Development of suckers | Very good |
| Position of suckers | Close to parent (vertical growth) |
| Blotches at the petiole base | Extensive pigmentation |
| Blotches color | Brown (200B, RHS) |
| Petiole canal leaf III | Wide with erect margins |
| Petiole margins | Winged and not clasping the pseudostem |
| Wing type | Dry |
| Entire Petiole color | Greyed-purple (187D, RHS) |
| Petiole margin color | Greyed-purple (187D, RHS) |
| Edge of petiole margin | Robust and Greyed-purple color (187D, RHS) |
| Petiole margin width | 1 to 2 cm |
| Leaf blade length | 171 to 220 cm |
| Leaf blade width | 71 to 80 cm |
| Petiole length | 40 to 50 cm |
| Color of the leaf's upper Surface | Green (139A, RHS) |
| Appearance of leaf upper surface | Shiny |
| Color of the leaf's lower surface | Green (139B, RHS) |
| The appearance of the leaf's lower surface | Dull |
| Leaf shape | Oval-elongated |
| Leaf apex | Obtuse |
| Leaf margin | Entire |
| Wax on leaves | Few waxes |
| The insertion point of the leaf blade on the petiole | Symmetric |
| The shape of the leaf blade base | Both sides rounded |
| Leaf corrugation | Even, smooth |
| Color of midrib dorsal surface | Green (139C, RHS) |
| Color of midrib ventral surface | Greyed-green (191B, RHS) |
| Color of cigar leaf dorsal surface | Yellow-green (144B, RHS) |
| Blotches on leaves of water suckers | Without blotches |
| Peduncle length | 61 to 70 cm |
| Empty nodes on the peduncle | Two or more |
| Peduncle width | 7-12 cm |
| Peduncle color | Green (139C, RHS) |
| Peduncle hairiness | Very hair, short hairs (similar to velvet touch) |
| Number of hands per bunch | 12 |
| Bunch length | 60 cm |
| Bunch diameter | 76 cm |
| Bunch position | Slightly angled |
| Bunch shape | Cylindrical |
| Bunch appearance | Compact |
| Flowers that form the fruit | Female |
| Fruits | Biseriate |
| Rachis type | Present and male buds may be degenerated or persistent |
| Rachis position | Failing vertically |
| Rachis appearance | Bare |
| Male bud type | Normal (present) |
| Male bud shape | Ovoid |
| Male bud size | Length: 28 cm and diameter 18 cm (at the widest section) |
| Bract base shape | Large shoulder |
| Bract apex shape | Ovoid |
| Bract imbrication | Young bracts considerably overlap. |
| Color of the bract external face | Purple (N79A, RHS) |
| Color of the bract internal ace | Red-purple (59B, RHS) |
| Color of the bract apex | Tinted with yellow (discolored) (154D, RHS) |
| Color stripes on the bract | Without discolored lines (not ridges) on the external face |
| Bract scars on rachis | Very prominent |
| Persistence of the bracts of the rachis | Moderate |
| Fading of color on bract base | Color homogenous |
| Male bract shape | Ovate |
| Male bract lifting | Lifting one at a time |
| Bract behavior before falling | Revolute (Rolling) |
| Wax on the bract | Moderately wax |
| Presence of grooves on the bract | Moderate |
| Male flower behavior | Falling before the bract |
| Compound tepals per flower | 6 |
| Compound tepal shape | Oval-elongated |
| Upper compound tepal basic color | White (155C, RHS) |
| Lower compound tepal color | Yellow-orange (19D, RHS) |
| Compound tepal length | 4.5 cm |
| Compound tepal width | 1.8 cm |
| Compound tepal pigmentation | Very few or no visible signs of pigmentation; pigmentation color which is present is yellow-orange (20D, RHS) |
| Upper lobe color of compound tepal | Yellow (13B, RHS) |
| Lower lobe color of compound tepal | Yellow (13D, RHS) |
| Lobe development of compound tepal | Developed |
| Free tepal color | Opaque White (155D, RHS) |
| Free tepal shape | Oval |
| Free tepal appearance | Several folding under apex (corrugated) |
| Free tepal apex development | Little or no visible sign of development |
| Free tepal apex shape | Thread-like |
| Anther exertion | Inserted |
| Filament color | Greyed-white (156B, RHS) |
| Anther color | Greyed-white (156C, RHS) |
| Pollen sacs color | Grey-brown (199D, RHS) |

-continued

| | |
|---|---|
| Pollen vitality | Abundant |
| Style basic color | Greyed-green (198D, RHS) |
| Pigmentation on style | Without pigmentation |
| Style exertion | Inserted |
| Style shape | Straight |
| Stigma color | Green-white (20B, RHS) |
| Ovary shape | Arched |
| Ovary basic color | Green-white (157C, RHS) |
| Ovary pigmentation | Very few or no visible sign of pigmentation; pigmentation color which is present is light green (149B, RHS) |
| The dominant color of male flower | White (155C, RHS) |
| Irregular flowers | Absent |
| Arrangement of ovules | Two rowed |
| Fruit position | Parallel to the stalk |
| Number of fruits | 17 to 20 |
| Fruit length | 13 to 15 cm |
| Fruit width | 3.5 cm |
| Fruit shape (longitudinal curvature) | Curved (sharp curve) |
| Color of the flesh of the fruit | Yellow (9A, RHS) |
| Longitudinal ridges of the fruit | Moderate |
| Transverse section of fruit | Rounded |
| Fruit apex | Bottle-necked |
| Remains of flower relicts at the fruit apex | Persistent style |
| Fruit pedicel length | 11 to 20 mm |

-continued

| | |
|---|---|
| Fruit pedicel width | 10 to 12 mm |
| Fruit pedicel color | Yellow-green (148A, RHS) |
| Pedicel surface | Hairy |
| Fusion of pedicel | Very partially or no visible sign of fusion |
| Immature fruit peel color | Green (141D, RHS) |
| Mature fruit peel color | Yellow-orange (17B, RHS) |
| Fruit peel thickness | 1.5 to 2 mm |
| Adherence to the fruit peel | Fruit peels easily |
| Cracks in fruit peel | Cracked |
| Pulp in fruit | With pulp |
| Pulp color before maturity | Greyed-white (156C, RHS) |
| Pulp color at maturity | White (155A, RHS) |
| Fruits fall from hands. | Persistent |
| Flesh texture | Firm |
| Predominant taste | Mild, slightly tasty, or tasteless |
| Presence of seed with the source of pollen | <5 |
| Seed surface | Smooth |
| Seed shape | Globular (spherical) |
| Seed color | Greyed-green (N189B, RHS) |
| Growth habit of the plant | Upright |

The invention claimed is:

1. A new and distinct variety of banana plant named 'WW01', substantially as illustrated and described herein.

* * * * *

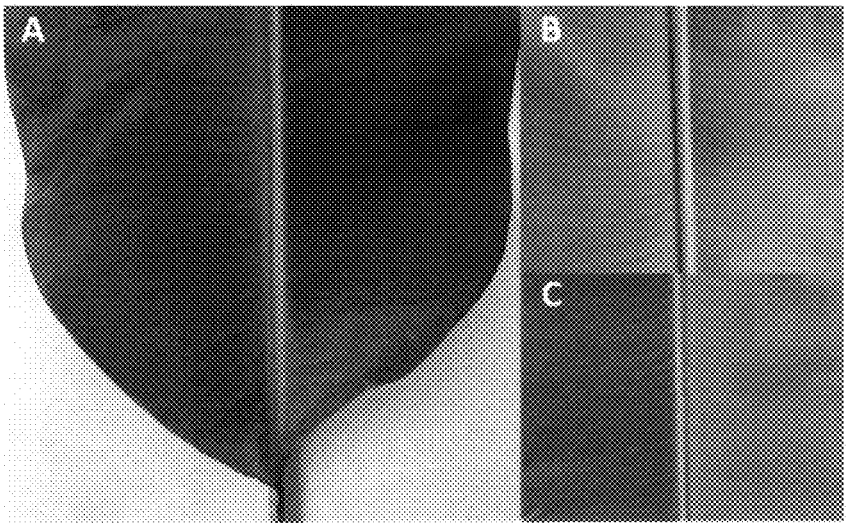
FIG. 3A, 3B, & 3C
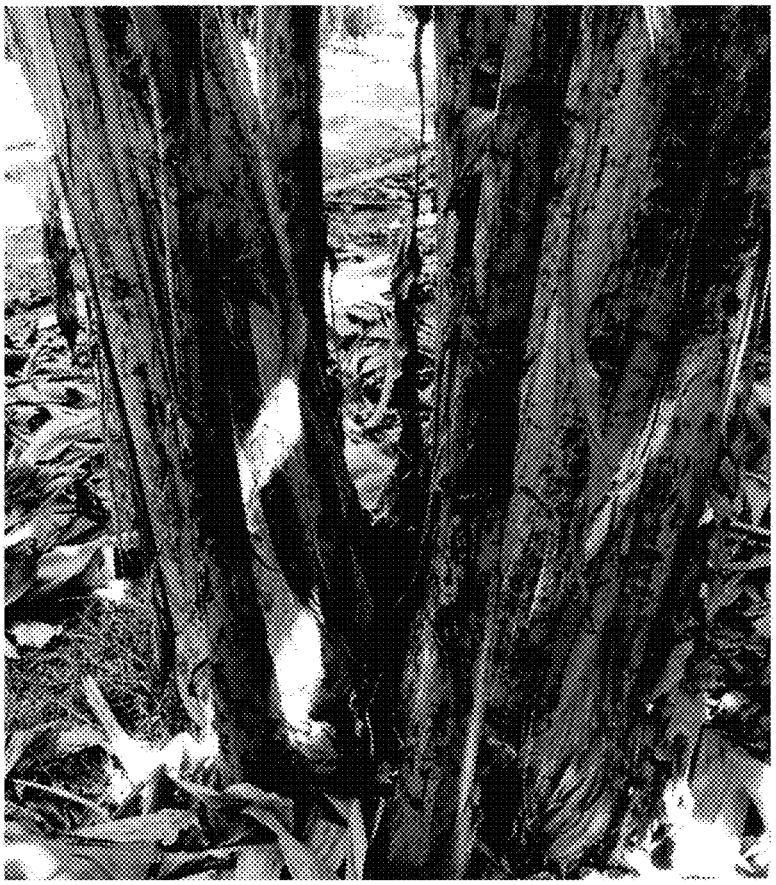
FIG. 4

FIG. 7A, 7B, & 7C